US011253501B2

(12) United States Patent
Palling et al.

(10) Patent No.: US 11,253,501 B2
(45) Date of Patent: *Feb. 22, 2022

(54) SECNIDAZOLE FORMULATIONS AND USE IN TREATING BACTERIAL VAGINOSIS

(71) Applicant: LUPIN INC., Baltimore, MD (US)

(72) Inventors: David Palling, Glen Ridge, NJ (US); Ronald S. Vladyka, Hillsborough, NJ (US); Joseph Amprey, Potomac, MD (US)

(73) Assignee: LUPIN INC., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/170,572

(22) Filed: Jun. 1, 2016

(65) Prior Publication Data

US 2016/0346252 A1 Dec. 1, 2016

Related U.S. Application Data

(60) Provisional application No. 62/169,369, filed on Jun. 1, 2015.

(51) Int. Cl.
*A61K 31/4164* (2006.01)
*A61K 9/50* (2006.01)
*A61K 31/454* (2006.01)
*A61K 31/5377* (2006.01)

(52) U.S. Cl.
CPC ........ *A61K 31/4164* (2013.01); *A61K 9/5031* (2013.01); *A61K 9/5042* (2013.01); *A61K 31/454* (2013.01); *A61K 31/5377* (2013.01)

(58) Field of Classification Search
None
See application file for complete search history.

(56) References Cited

U.S. PATENT DOCUMENTS

| | | | |
|---|---|---|---|
| 3,376,311 A | | 4/1968 | Butler |
| 4,920,141 A | | 4/1990 | Hortstmann et al. |
| 4,925,950 A | | 5/1990 | Massonneau et al. |
| 4,925,951 A | | 5/1990 | Massonneau et al. |
| 4,925,952 A | | 5/1990 | Massonneau et al. |
| 4,957,918 A | | 9/1990 | Martin et al. |
| 5,023,361 A | | 6/1991 | Massonneau et al. |
| 5,026,694 A | | 6/1991 | Skov et al. |
| 5,140,055 A | | 8/1992 | Hirata et al. |
| 5,329,003 A | | 7/1994 | Bruchmann |
| 5,549,911 A | † | 8/1996 | Leduc |
| 5,574,167 A | | 11/1996 | Jaber |
| 5,614,545 A | | 3/1997 | Martin et al. |
| 5,904,937 A | * | 5/1999 | Augello ............... A61K 9/0056 424/441 |
| 6,103,262 A | | 8/2000 | Desai et al. |
| 6,214,386 B1 | | 4/2001 | Santus et al. |
| 6,653,333 B2 | * | 11/2003 | Yotsuya ................ A61K 31/44 514/352 |
| 6,794,372 B2 | | 9/2004 | Del Soldato et al. |
| 7,485,729 B2 | | 2/2009 | Hsieh et al. |
| 7,691,831 B2 | | 4/2010 | Bonner, Jr. et al. |
| 7,884,090 B2 | | 2/2011 | Bonner, Jr. et al. |
| 7,893,097 B2 | | 2/2011 | Yang et al. |
| 8,088,846 B2 | | 1/2012 | Hsieh et al. |
| 8,158,152 B2 | | 4/2012 | Palepu |
| 8,309,103 B2 | | 11/2012 | Hernandez-Ramirez et al. |
| 8,658,678 B2 | | 2/2014 | Yang et al. |
| 8,772,242 B2 | | 7/2014 | Borody |
| 8,853,247 B2 | | 10/2014 | Ren et al. |
| 8,877,792 B2 | | 11/2014 | Yang et al. |
| 8,946,276 B2 | | 4/2015 | Nordsiek et al. |
| 8,999,360 B2 | | 4/2015 | Borody et al. |
| 9,016,221 B2 | | 4/2015 | Brennan et al. |
| 2003/0017210 A1 | | 1/2003 | Debregeas et al. |
| 2003/0091540 A1 | | 5/2003 | Ahmad et al. |
| 2003/0092754 A1 | | 5/2003 | Nishimuta et al. |
| 2004/0033968 A1 | | 2/2004 | Lin et al. |
| 2004/0247675 A1 | * | 12/2004 | Gruber ................ A61K 9/0056 424/471 |
| 2005/0026982 A1 | | 2/2005 | Johannsen et al. |
| 2005/0133283 A1 | | 5/2005 | Solow-Cordero et al. |
| 2005/0165077 A1 | | 7/2005 | Hernandez-Ramirez et al. |
| 2005/0186142 A1 | | 8/2005 | Tamarkin et al. |
| 2005/0214364 A1 | | 9/2005 | Hutman et al. |
| 2005/0222169 A1 | | 10/2005 | Ahmad et al. |
| 2006/0024243 A1 | | 2/2006 | Arkin et al. |
| 2006/0137684 A1 | | 6/2006 | Evans et al. |

(Continued)

FOREIGN PATENT DOCUMENTS

| | | |
|---|---|---|
| CN | 1421438 A | 6/2003 |
| CN | 1442410 A | 9/2003 |

(Continued)

OTHER PUBLICATIONS

Lamp et al. (Pharmacokinetics and pharmacodynamics of the nitoimidazole antimicrobials), Clin. Pharmacokinetics, May 1999; 36 (5): 353-373. (Year: 1999).*

Lelievre et el. "Pharmacokinetics of secnidazole in healthy volunteers after single oral dose", 2010 (Year: 2010).*

Lamp et al. "Pharmacokinetics and pharmacodynamics of the nitoimidazole antimicrobials", Clinical Pharmacokinetic; May 1999, 36(5), 353-373. (Year: 1999).*

Amsel et al., "Nonspecific vaginitis: Diagnostic criteria and microbial and epidemiologic associations," *Am. J. Med.* (Jan. 1983) 74(1):14-22.

(Continued)

*Primary Examiner* — Isis A Ghali

(74) *Attorney, Agent, or Firm* — Duane Morris LLP

(57) ABSTRACT

Embodiments described herein are directed to novel pharmaceutical compositions comprising a plurality of microgranules comprising nitroimidazole compounds, and uses of these pharmaceutical compositions in the treatment of bacterial vaginosis.

18 Claims, No Drawings

(56) References Cited

U.S. PATENT DOCUMENTS

| | | |
|---|---|---|
| 2006/0140984 A1 | 6/2006 | Tamarkin et al. |
| 2006/0140990 A1 | 6/2006 | Bortz et al. |
| 2007/0015841 A1 | 1/2007 | Tawa et al. |
| 2007/0154516 A1 | 7/2007 | Bortz et al. |
| 2007/0255064 A1 | 11/2007 | Szarvas et al. |
| 2007/0287714 A1 | 12/2007 | Ahmad et al. |
| 2008/0139664 A1 | 6/2008 | Yeboah et al. |
| 2008/0171709 A1 | 7/2008 | Remmal |
| 2008/0171768 A1 | 7/2008 | Remmal |
| 2009/0131342 A1 | 5/2009 | Ellis |
| 2010/0159035 A1 | 6/2010 | Shemer |
| 2010/0304998 A1 | 12/2010 | Sem |
| 2011/0046378 A1 | 2/2011 | Kolb et al. |
| 2012/0219500 A1 | 8/2012 | Sakurai et al. |
| 2012/0295839 A1 | 11/2012 | Paull et al. |
| 2013/0309219 A1† | 11/2013 | Ratner |
| 2014/0065230 A1 | 3/2014 | Shah et al. |
| 2014/0080778 A1 | 3/2014 | Defrance |
| 2014/0271923 A1 | 9/2014 | Reid |
| 2015/0196536 A1 | 7/2015 | Yang et al. |
| 2016/0067218 A1 | 3/2016 | Pentikis et al. |

FOREIGN PATENT DOCUMENTS

| | | | |
|---|---|---|---|
| CN | 1546020 A | 11/2004 | |
| CN | 1789250 A | 6/2006 | |
| CN | 1973838 A * | 6/2007 | |
| CN | 101108828 A | 1/2008 | |
| CN | 101255175 A | 9/2008 | |
| CN | 102335433 A * | 2/2012 | |
| EP | 1712229 A1 | 10/2006 | |
| GN | 101874799 A | 11/2010 | |
| WO | 19951020383 A1 | 8/1995 | |
| WO | WO-2012075015 A2 * | 6/2012 | ........... A61K 9/2846 |
| WO | 2012151237 A1 | 11/2012 | |
| WO | WO2014/121298 A2 | 8/2014 | |
| WO | WO2016/037131 | 3/2016 | |
| WO | 2016196653 A1 | 12/2016 | |

OTHER PUBLICATIONS

Nugent et al., "Reliability of Diagnosing Bacterial Vaginosis Is Improved by a Standardized Method of Gram Stain Interpretation," *J. Clin. Microbiol.* (Feb. 1991), 29(2):297-301.
Acar et al., "Le secnidazole, un nouveau 5-nitro-imidazolé," 2005, *Antibiotiques* (2005); 7:177-182.
Gillis, "Secnidazole. A review of its antimicrobial activity, pharmokinetic properties and therapeutic use in the management of protozoal infections and bacterial vaginosis," *Drugs* (1996), 51(4):621-638.
Hangargekar et al., "Formulation and Evaluation of Guar Gum Based Colon Targeted Tablets of Secnidazole and Its β-Cyclodextrin Complex to Treat Amoebiasis," *Int'l J. Pharmacy and Pharmaceutical Sciences* (2011), 3(4):294-298.
International Search Report and Written Opinion for PCT/US2015/048681 dated Jan. 19, 2016.
International Search Report and Written Opinion for PCT/US2016/035299 dated Aug. 22, 2016.
Malholtra, "Ciprofloxacin-tinidazol combination, fluconazole-azithromycin-secnidazole-kit and doxycycline-metronidazole combination therapy in syndromic management of pelvic imflammatory disease," *Indian J. Medicinal Sciences* (Dec. 1, 2003), 57(12):549-555.
Menard, "Antibacterial treatment of bacterial vaginosis: current and emerging therapies," *Int'l J. Women's Health* (2011), 3:295-305.
Narayana et al., "Formulation and In Vitro Evaluation of In Situ Gels Containing Secnidazole for Vaginitis," *Yakugaku Zasshi* (2009), 129(5):569-574.
Bohbot et al., Treatment of Bacterial Vaginonis: A Multicenter, Double-Blind, Double-Dummy, Randomised Phase III Study Comparing Secnidazole and Metronidazole, Infec. Dis. Obs. Gynecol., Hindawi Publishing Corp. (2010) Art. 705692.
Núñez et al., Low-dose secnidazole in the treatment of bacterial vaginosis, Int'l J. Gyne. Obst. (2004), 88:281-285.
Material Safety Data Sheet—Avicel® PH Microcrystalline Cellulose, FMC Corporation (May 27, 2014).
Material Safety Data Sheet—METHOCEL A15 Premium LV Methylcellulose, The Dow Chemical Company (Jan. 12, 2007).
R.K. Chang, et al., "Polymethacrylates," R.C. Rowe, P.J. Sheskey (Eds.), Handbook of Pharmaceutical Excipients, Pharmaceutical Press, London, pp. 525-533 (2009).
Observation of Third-Party in PCT/US2016/035299 submitted Sep. 27, 2017.
Debacker et al., In vitro activity of secnidazole against Atopobium vaginae, an anaerobic pathogen involved in bacterial vaginosis, Clin. Micobiol. Infect. (Jun. 22, 2009); 16:470-472.

\* cited by examiner
† cited by third party

SECNIDAZOLE FORMULATIONS AND USE IN TREATING BACTERIAL VAGINOSIS

CROSS REFERENCE RELATED APPLICATIONS

This application claims the benefit of priority to U.S. Provisional Application No. 62/169,369 entitled "Novel Nitroimidazole Formulations And Uses Thereof" filed Jun. 1, 2015; the disclosure of which is incorporated by reference in its entirety.

SUMMARY

Embodiments herein are directed to pharmaceutical compositions comprising a plurality of microgranules, wherein the microgranules comprise a core and a coating; wherein the core comprises a nitroimidazole compound or pharmaceutically acceptable salt thereof; and wherein the coating surrounds the core. In some embodiments, the nitroimidazole compound is selected from secnidazole, metronidazole, tinidazole, nimorazole, dimetridazole, 6-Amino PA824, ornidazole, megazol, azanidazole, benznidazole, pimonidazole, and combinations thereof. In some embodiments, the nitroimidazole compound is secnidazole. In some embodiments, the nitroimidazole compound comprises at least about 70% of the core by weight. In some embodiments, the nitroimidazole compound comprises about 70% of the core by weight. In some embodiments, the plurality of microgranules comprise about 1 gram to about 2 grams of the nitroimidazole compound. In some embodiments, the plurality of microgranules comprise a therapeutically effective amount of the nitroimidazole compound. In some embodiments, the core further comprises at least one polymer. In some embodiments, the polymer is selected from Avicel®, Methocel®, hydroxyl propyl cellulose, acacia, guar gum, povidone, lactose monohydrate, and any combination thereof. In some embodiments, the core further comprises Avicel and Methocel. In some embodiments, the core further comprises Avicel pH101 and Methocel AV15LV. In some embodiments, the polymer comprises about 30% of the core by weight. In some embodiments, the coating comprises a polymer. In some embodiments, the polymer is selected from Eudagrit®, ethyl cellulose, methocel, glyceryl behenate, and any combination thereof. In some embodiments, the polymer is Eudagrit NE30D. In some embodiments, the coating further comprises a polyether polymer. In some embodiments, the polyether polymer is selected from polyethylene glycol, acetyl tributyl citrate, triethyl citrate, dibutyl phthalate, dibutyl sebacate, gelatin, propelyne glycol, triacetin, and any combination thereof. In some embodiments, the polyether polymer is PEG 4000. In some embodiments, the coating further comprises talc. In some embodiments, the coating comprises about 13% of the composition by weight. Some embodiments further comprise talc. In some embodiments, the core comprises a spheronized microgranule. In some embodiments, the core further comprises a binder.

Some embodiments are directed to methods of treating bacterial vaginosis in patient comprising administering to the patient a pharmaceutical composition comprising a plurality of microgranules, wherein the microgranules comprise a core and a coating; wherein the core comprises therapeutically effective amount of a nitroimidazole compound or pharmaceutically acceptable salt thereof; and wherein the coating surrounds the core. In some embodiments, the nitroimidazole compound is selected from secnidazole, metronidazole, tinidazole, nimorazole, dimetridazole, 6-Amino PA824, ornidazole, megazol, azanidazole, benznidazole, pimonidazole, and combinations thereof. In some embodiments, the nitroimidazole compound is secnidazole. In some embodiments, the nitroimidazole compound comprises at least about 70% of the core by weight. In some embodiments, the nitroimidazole compound comprises about 70% of the core by weight. In some embodiments, the plurality of microgranules comprise about 1 gram to about 2 grams of the nitroimidazole compound. In some embodiments, the core further comprises at least one polymer. In some embodiments, the polymer is selected from Avicel, Methocel, hydroxyl propyl cellulose, acacia, guar gum, povidone, lactose monohydrate, and any combination thereof. In some embodiments, the core further comprises Avicel and Methocel. In some embodiments, the core further comprises Avicel pH101 and Methocel AV15LV. In some embodiments, the polymer comprises about 30% of the core by weight. In some embodiments, the coating comprises a polymer. In some embodiments, the polymer is selected from Eudagrit®, ethyl cellulose, methocel, glyceryl behenate, and any combination thereof. In some embodiments, the polymer is Eudagrit NE30D. In some embodiments, the coating further comprises a polyether polymer. In some embodiments, the polyether polymer is selected from polyethylene glycol, acetyl tributyl citrate, triethyl citrate, dibutyl phthalate, dibutyl sebacate, gelatin, propelyne glycol, triacetin, and any combination thereof. In some embodiments, the polyether polymer is PEG 4000. In some embodiments, the coating further comprises talc. In some embodiments, the coating comprises about 13% of the composition by weight. Some embodiments further comprise talc. In some embodiments, the core comprises a spheronized microgranule. In some embodiments, the core further comprises a binder.

DETAILED DESCRIPTION

Embodiments described herein are directed to novel pharmaceutical compositions comprising a plurality of microgranules; wherein the microgranules comprise a core and a coating; wherein the core comprises a nitroimidazole compound or pharmaceutically acceptable salt thereof; and wherein the coating surrounds the core. In some embodiments, the pharmaceutical compositions described herein are designed for oral administration.

Current nitroimidazole drugs such as secnidazole are effective in the treatment of several conditions including bacterial vaginosis. However, the dosages required for treatment and the current formulations mean that very large amount of the drug must be taken by a patient which raises the risk of non-compliance by patients and the exclusion of certain patients not able to ingest the amount of drug required. Applicant has developed novel pharmaceutical compositions comprising microgranules that allow for therapeutic dosing in smaller unit doses thus addressing the problems caused by the conventional drug formulations and high doses required for therapeutic effectiveness.

Before the present formulations and methods are described, it is to be understood that this invention is not limited to the particular processes, compounds, or methodologies described, as these may vary. It is also to be understood that the terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety.

In each of the embodiments disclosed herein, the compounds and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "patient" and "subject" are interchangeable and may be taken to mean any living organism, which may be treated with compounds of the present invention. As such, the terms "patient" and "subject" may include, but is not limited to, any non-human mammal, primate or human. In some embodiments, the "patient" or "subject" is an adult, child, infant, or fetus. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

As used herein, the terms "adjunctive administration" and "adjunctively" may be used interchangeably, and refer to simultaneous administration of more than one compound in the same dosage form, simultaneous administration in separate dosage forms, and separate administration of more than one compound as part of a single therapeutic regimen.

It must be noted that, as used herein, and in the appended claims, the singular forms "a", "an" and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the described includes instances where the event occurs and instances where it does not.

"Administering" when used in conjunction with a therapeutic means to administer a therapeutic directly or indirectly into or onto a target tissue to administer a therapeutic to a patient whereby the therapeutic positively impacts the tissue to which it is targeted. "Administering" a composition may be accomplished by oral administration, injection, infusion, inhalation, absorption or by any method in combination with other known techniques. "Administering" may include the act of self-administration or administration by another person such as a health care provider.

As used here, the term "therapeutic" means an agent utilized to treat, combat, ameliorate or prevent an unwanted disease, condition or disorder of a patient.

The terms "therapeutically effective amount" or "therapeutic dose" is used herein are interchangeable and may refer to the amount of an active agent or pharmaceutical compound or composition that elicits a clinical, biological or medicinal response in a tissue, system, animal, individual or human that is being sought by a researcher, veterinarian, medical doctor or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experience or exhibited by the individual.

As used herein, the term "daily dose amount" refers to the amount of an active agent per day that is administered or prescribed to a patient. This amount can be administered in multiple unit doses or in a single unit dose, in a single time during the day or at multiple times during the day.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain secnidazole or a pharmaceutically acceptable salt of secnidazole as the active ingredient.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail. A pharmaceutical acceptable "salt" is any acid addition salt, preferably a pharmaceutically acceptable acid addition salt, including, but not limited to, halogenic acid salts such as hydrobromic, hydrochloric, hydrofloric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesufonic, acetic, malic, fumaric, succinic, citric, benzonic gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

Embodiments described herein are directed to novel pharmaceutical compositions comprising a plurality of microgranules; wherein the microgranules comprise a core and a coating; wherein the core comprises a nitroimidazole compound or pharmaceutically acceptable salt thereof; and wherein the coating surrounds the core. In some embodiments, the pharmaceutical compositions described herein are designed for oral administration. In some embodiments, the core comprises therapeutically effective amount of a nitroimidazole compound or pharmaceutically acceptable salt thereof.

In some embodiments, the plurality of microgranules may be contained, or encased in a sachet, a capsule (soft shell or hard shell capsule), a gel cap, or any other suitable encapsulation medium known in the art. In some embodiments, the plurality of microgranules may be configured as a powder for reconstitution as a suspension. In some embodiments, a plurality of microgranules corresponding to a therapeutically effective amount of the nitroimidazole may be encased, or encapsulated in one or more sachets, capsules (soft shell or hard shell capsule), gel caps, or any other suitable encapsulation mediums known in the art. For example, in some embodiments, the plurality of microgranules will be sufficient to provide 2 gram of secnidazole in the pharmaceutical composition.

Some embodiments are directed to a microgranule comprising a core and a coating; wherein the core comprises an amount of a nitroimidazole compound or pharmaceutically acceptable salt thereof; and wherein the coating surrounds the core. In some embodiments, the amount of a nitroimidazole compound or pharmaceutically acceptable salt thereof may be a therapeutically effective amount of a nitroimidazole compound or pharmaceutically acceptable salt thereof. In some embodiments, the amount of a nitroimidazole compound or pharmaceutically acceptable salt thereof may be a portion of a therapeutically effective amount of a nitroimidazole compound or pharmaceutically acceptable salt thereof. For example, a microgranule may comprise about 0.17 milligrams of secnidazole, wherein a therapeutically effective amount of secnidazole is about 2 grams. Accordingly, microgranules may combined in a pharmaceutical composition to achieve a therapeutically effective amount secnidazole. In some embodiments, the amount of a nitroimidazole compound or pharmaceutically acceptable salt thereof may be a daily dose amount of a nitroimidazole compound or pharmaceutically acceptable salt thereof. In some embodiments, the amount of a nitroimidazole compound or pharmaceutically acceptable salt thereof may be a portion of a daily dose amount of a nitroimidazole compound or pharmaceutically acceptable salt thereof. For example, a microgranule may comprise about 0.17 milligrams of secnidazole, wherein a daily dose amount of secnidazole is about 2 grams. Accordingly, microgranules may combined in a pharmaceutical composition to achieve a daily dose amount of secnidazole.

Some embodiments are directed to a plurality of microgranules comprising a daily dose amount of a nitroimidazole compound. In some embodiments, the plurality of microgranules collectively comprising a daily dose amount of a nitroimidazole compound may be configured as a single unit dose. In some embodiments, the plurality of microgranules collectively comprising a daily dose amount of a nitroimidazole compound may be configured as multiple unit doses. In some embodiments, the plurality of microgranules collectively comprising a daily dose amount of a nitroimidazole compound may be configured as one, two, three or four unit doses. Accordingly, the plurality of microgranules may comprise a portion of the daily dose amount of a nitroimidazole compound. In some embodiments, the nitroimidazole compound is secnidazole and the daily dose amount is about 1 to about 2 grams. In some embodiments, the nitroimidazole compound is secnidazole and the daily dose amount is about 2 grams. In some embodiments, the plurality of microgranules collectively comprising a daily dose amount of secnidazole may be configured as one, two, three or four unit doses. For example, the plurality of microgranules comprising about 2 grams of secnidazole may be configured as 2 unit doses, each unit dose comprising about 1 gram of secnidazole. Likewise, the plurality of microgranules comprising about 2 grams of secnidazole may be configured as 4 unit doses, each unit dose comprising about 0.5 grams of secnidazole.

In some embodiments, the plurality of microgranules collectively comprise a therapeutically effective amount of a nitroimidazole compound. This amount can be administered in multiple unit doses or in a single unit dose, in a single time during the day or at multiple times during the day. In some embodiments, the plurality of microgranules collectively comprising a therapeutically effective amount of a nitroimidazole compound may be configured as a single unit dose. In some embodiments, the plurality of microgranules collectively comprising a therapeutically effective amount of a nitroimidazole compound may be configured as a multiple unit doses. In some embodiments, the plurality of microgranules collectively comprising a therapeutically effective amount of a nitroimidazole compound may be configured as one, two, three or four unit doses. Accordingly, the plurality of microgranules may comprise a portion of the therapeutically effective amount of a nitroimidazole compound. In some embodiments, the nitroimidazole compound is secnidazole and the therapeutically effective amount is about 1 to about 2 grams. In some embodiments, the nitroimidazole compound is secnidazole and the therapeutically effective amount is about 2 grams. In some embodiments, the plurality of microgranules collectively comprising a therapeutically effective amount of secnidazole may be configured as one, two, three or four unit doses. For example, the plurality of microgranules comprising about 2 grams of secnidazole may be configured as 2 unit doses, each unit dose comprising about 1 gram of secnidazole. Likewise, the plurality of microgranules comprising about 2 grams of secnidazole may be configured as 4 unit doses, each unit dose comprising about 0.5 grams of secnidazole. Accordingly, the plurality of microgranules may comprise a portion of the therapeutically effective amount of secnidazole.

The pharmaceutical compositions described herein may be prepared, packaged, or sold in bulk, as a single unit dose or as multiple unit doses and may be administered in the conventional manner by any route where they are active.

In some embodiments, therapeutically effective amounts, daily doses, or single unit doses of the nitroimidazole compositions described herein may be administered once per day or multiple times per day, such as 1 to 5 doses, twice per day or three times per day.

Embodiments are also directed to a dosage regimen for administering a nitroimidazole compound to treat the conditions disclosed herein. For example, in some embodiments, the methods described herein may comprise a dosage regimen that may include a plurality of daily doses having an equal amount of a nitroimidazole compound as the initial dose in one or more unit doses. In other embodiments, the dosage regimen may include an initial dose of a nitroimidazole compound in one or more unit doses, then a plurality of daily doses having a lower amount of a nitroimidazole compound as the initial dose in one or more unit doses. The dosage regimen may administer an initial dose followed by one or more maintenance doses. The plurality of doses following the administering of an initial dose may be maintenance doses.

In some embodiments, the plurality of microgranules collectively comprise multiple daily dose amounts. In some embodiments, the plurality of microgranules collectively comprise multiple therapeutically effective amounts. For example, in some embodiments, the daily dose amount of secnidazole is 2 grams, and the plurality of microgranules may comprise 200 grams of secnidazole which represents 100 daily dose doses of secnidazole. In some embodiments, the nitroimidazole compound is selected from secnidazole, metronidazole, tinidazole, nimorazole, dimetridazole, 6-Amino PA824, ornidazole, megazol, azanidazole, benznidazole, pimonidazole, and combinations thereof. In some embodiments, the nitroimidazole compound is secnidazole [1-(2-hydroxypropyl)-2-methyl-5-nitromidazole].

In some embodiments, the nitroimidazole compound comprises at least about 70% of the core by weight. In some embodiments, the nitroimidazole compound comprises at least about 75% of the core by weight. In some embodiments, the nitroimidazole compound comprises at least about 80% of the core by weight. In some embodiments, the nitroimidazole compound comprises at least about 85% of the core by weight. In some embodiments, the nitroimidazole compound comprises at least about 90% of the core by weight. In some embodiments, the nitroimidazole compound comprises at least about 95% of the core by weight. In some embodiments, the nitroimidazole compound comprises about 70% of the core by weight. In some embodiments, the nitroimidazole compound comprises about 75% of the core by weight. In some embodiments, the nitroimidazole compound comprises about 80% of the core by weight. In some embodiments, the nitroimidazole compound comprises about 85% of the core by weight. In some embodiments, the nitroimidazole compound comprises about 90% of the core by weight. In some embodiments, the nitroimidazole compound comprises about 95% of the core by weight.

In some embodiments, the microgranules described herein allow for increased drug loading such that higher doses of a drug may be delivered to a patient in a pharmaceutical composition that may have a smaller total mass than with a conventional drug coated sugar core composition. For example, in some embodiments, the nitroimidazole compound may comprise up to about 70% of the core by weight without loss of the spherical shape of the individual microgranules. Accordingly, a plurality of microgranules wherein the nitroimidazole compounds comprises about 70% of the core by weight may represent an optimal balance between the desired physical characteristics of the microgranules and an increased drug load to reduce the overall mass of the composition required to administer a desired dose. However, in some embodiments, the nitroimidazole compound may comprise up to about 80% of the core by weight without loss of the spherical shape of the individual microgranules. In some embodiments, the nitroimidazole compound may comprise up to about 90% of the core by weight without loss of the spherical shape of the individual microgranules, the nitroimidazole compound may comprise greater than 90% of the core by weight without loss of the spherical shape of the individual microgranules.

In some embodiments, the plurality of microgranules comprises a therapeutically effective amount of the nitroimidazole compound. In some embodiments, the plurality of microgranules comprises a therapeutically effective amount of secnidazole. In some embodiments, the plurality of microgranules comprises about 1 gram to about 2 grams of the nitroimidazole compound. In some embodiments, the plurality of microgranules comprises about 2 grams of the nitroimidazole compound. In some embodiments, the plurality of microgranules comprises about 1 gram to about 2 grams of secnidazole. In some embodiments, the plurality of microgranules comprises about 2 grams of secnidazole.

In some embodiments, the core further comprises at least one polymer. In some embodiments, the polymer is selected from Avicel®, Methocel®, hydroxyl propyl cellulose, acacia, guar gum, povidone, lactose monohydrate, and any combination thereof. In some embodiments, the at least one polymer may comprise about 30% of the core by weight. In some embodiments, the polymer may comprise less than about 30% of the core by weight. In some embodiments, the core further comprises Avicel® and Methocel. In some embodiments, the core further comprises Avicel® pH101 and Methocel® AV15LV. In some embodiments, the Avicel® pH101 comprises about 22.84% of the core by weight. In some embodiments, the Methocel® AV15LV comprises about 3.02% of the core by weight. For example, in some embodiments, the core may comprise about 70% secnidazole, about 22.84% Avicel® pH101, and about 3.02% Methocel® AV15LV by weight. In some embodiments, the ratio of the nitroimidazole to polymer in the core may be less than 70%. Accordingly, a plurality of microgranules comprising a 2 gram dose of secnidazole, wherein the secnidazole represents about 70% of the microgranule core, may additionally comprise about 757 grams of Avicel® pH101, and about 100 grams of Methocel® AV15LV. In some embodiments, the ratio of the nitroimidazole to polymer in the core may be about 70:30. In some embodiments, the ratio of the nitroimidazole to polymer in the core may be less than about 70:30. In some embodiments, the ratio of the nitroimidazole to polymer in the core may be greater than about 70:30.

In some embodiments, the core may additionally contain a lubricant such as but not limited to sodium stearate, magnesium stearate, stearic acid, talc or a combination thereof.

In some embodiments, the microgranule coating comprises about 13% of the composition by weight. In some embodiments, the coating may comprise less than about 13% of the composition by weight. In some embodiments, the coating may comprise about 10% of the composition by weight. In some embodiments, the coating may comprise about 10% or more, of the composition by weight. In some embodiments, the coating may be modified to modulate drug absorption of the drug by varying the composition of the coating, the percentage weight of the composition, or any combination thereof. In some embodiments, the coating comprises a polymer. In some embodiments, the polymer may be selected from the group consisting of polyvinylpyrrolidone, ethylcellulose, Eudragit® RL, Eudragit® L, Eudragit® E, Eudragit® S, cellulose acetate, polyvinyl alcohol, shellac, methacrylic acid copolymers, cellulose acetate phthalate, hydroxypropylmethylcellulose phthalate, hydroxypropylmethylcellulose acetate succinate, cellulose acetate trimellitate and polyvinyl acetate phthalate. In some embodiments, the polymer is selected from Eudagrit, ethyl cellulose, methocel, glyceryl behenate, and any combination thereof. In some embodiments, the polymer is Eudagrit® NE30D. In some embodiments, the Eudagrit® NE3OD comprises about 5.795% of the composition by weight.

In some embodiments, the coating further comprises a polyether polymer. In some embodiments, the polyether polymer is selected from polyethylene glycol, acetyl tributyl citrate, triethyl citrate, dibutyl phthalate, dibutyl sebacate, gelatin, propelyne glycol, triacetin, and any combination thereof. In some embodiments, the polyether polymer is PEG 4000. In some embodiments, the PEG 4000 comprises about 1.75% of the composition by weight. In some embodiments, the PEG 4000 comprises about 1.75% of an individual microgranule by weight.

In some embodiments, other auxiliary coating aids such as a minor amount (about 1 to about 5% by weight based on the active core component and the total weight of the final coating) of a plasticizer such as, but not limited to acetyltributyl citrate, triacetin, acetylated monoglyceride, grape seed oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol, propylene glycol and mixtures thereof in combination with an antisticking agent which may be a silicate such as talc. In some embodiments, the coating further comprises talc.

In some embodiments, the composition further comprises talc. In some embodiments, the plurality of microgranules further comprises talc. In some embodiments, the talk acts as a blending agent.

In some embodiments, the core comprises a spheronized microgranule. In some embodiments, the microgranules may be formed by wet granulation followed by extrusion and spheronization. In some embodiments, the core further comprises a binder. In some embodiments, the binder may be starch.

Some embodiments are directed to a pharmaceutical composition comprising secnidazole microgranules formulated as shown in Table 1. The experimental microgranule compositions described in Table 1 allow for increased drug loading (70%) versus drug loading of a conventional secnidazole-coated sugar sphere formulation (about 49%). The ability to increase drug loading of the microgranules for use in the compositions and methods described herein enables a therapeutic dose of a nitroimidazole compound, for example, 2 grams of secnidazole, to be administered in a composition with a substantially reduced mass (about 3,315 mg) compared with the mass of a secnidazole-coated sugar sphere formulation (about 4,600 mg) while maintaining substantially the same pharmacokinetic profile upon administration of a 2 gram dose to a patient. In some embodiments, a 2 gram dose as in Table 1 can be incorporated into about 4 size "00" capsules compared with 6 size "00" capsules for the coated secnidazole-coated sugar sphere formulation. In some embodiments, drug loading of the microgranules may exceed 70%, such as, for example, 90% drug loading in which case, a 2 gram dose of secnidazole may be incorporated into about 4 size "0EL" capsules.

TABLE 1

Experimental high drug loading formulation

| Material | mg/dose | % w/w |
|---|---|---|
| Drug Core | | |
| Secnidazole | 2000.00 | 60.33 (70.00% of core) |
| Avicel pH 101 | 757.00 | 22.84 (26.50% of core) |
| Methocel AV15LV | 100.00 | 3.02 (3.50% of core) |

TABLE 1-continued

Experimental high drug loading formulation

| Material | mg/dose | % w/w |
|---|---|---|
| Finish Coating | | |
| Eudragit NE30D | 192.00 | 5.79 |
| PEG 4000 | 58.00 | 1.75 |
| Talc USP | 192.00 | 5.79 |
| Blending | | |
| Talc USP | 16.00 | 0.48 |
| Total Weight | 3315.00 | 100.0 |

In some embodiments, the pharmaceutical compositions described herein comprising the secnidazole microgranules may exhibit a similar pharmacokinetic profile as a coated secnidazole-coated sugar sphere formulated as shown in Table 2.

TABLE 2

Coated secnidazole-coated sugar sphere formulation

| Material | mg/dose | % w/w |
|---|---|---|
| Secnidazole | 2000.00 | 43.48 |
| Sugar Spheres (size 40-50 mesh) | 2000.00 | 43.48 |
| Povidone (Plasdone K-29/32) | 81.63 | 1.77 |
| Polyethylene Glycol 4000 | 83.3 | 1.81 |
| Eudragit NE30D (Ethyl Acrylate, Methyl Methacrylate Copolymer | 277.6621 | 6.04 |
| Talc | 138.831 | 3.02 |
| Colloidal Silicon Dioxide (Aerosil 200) | 18.577 | 0.40 |
| Total | 4600.00 | 100 |

In some embodiments, the pharmaceutical compositions described herein may have a pharmacokinetic profile comparable to the profiles shown in Tables 3 and 4, which display the pharmacokinetic profile of the composition of Table 2.

TABLE 3

Expected Plasma Pharmacokinetics of 2 gram secnidazole microgranule formulation (70% drug in microgranule core) after a single oral dose administered to fasted healthy female subjects

| Parameter | Secnidazole 2 grams (N = 14) |
|---|---|
| $C_{max}$ (µg/mL) | |
| n | 14 |
| Mean (SD) | 45.43 (7.642) |
| % CV | 16.82 |
| Geometric Mean (SD) | 44.84 (7.467) |
| Median | 45.05 |
| Min, Max | 34.5, 58.3 |
| $T_{max}$ (h) | |
| n | 14 |
| Median | 4.000 |
| Min, Max | 3.00, 4.05 |
| $AUC_{0-t}$ (h*µg/mL) | |
| n | 14 |
| Mean (SD) | 1322.40 (230.256) |
| % CV | 17.41 |
| Geometric Mean (SD) | 1305.35 (214.383) |

TABLE 3-continued

Expected Plasma Pharmacokinetics of 2 gram secnidazole microgranule formulation (70% drug in microgranule core) after a single oral dose administered to fasted healthy female subjects

| Parameter | Secnidazole 2 grams (N = 14) |
|---|---|
| Median | 1290.41 |
| Min, Max | 1048.5, 1899.5 |
| $AUC_{0-\infty}$ (h*µg/mL) | |
| n | 14 |
| Mean (SD) | 1331.63 (230.159) |
| % CV | 17.28 |
| Geometric Mean (SD) | 1314.74 (214.081) |
| Median | 1299.10 |
| Min, Max | 1055.1, 1911.9 |
| $t_{1/2}$ (h) | |
| n | 14 |
| Mean (SD) | 16.86 (2.649) |
| Median | 17.13 |
| Min, Max | 11.3, 20.4 |
| $\lambda z$ (1/h) | |
| n | 14 |
| Mean (SD) | 0.04220 (0.007544) |
| Median | 0.04047 |
| Min, Max | 0.0340, 0.0613 |

TABLE 4

Expected Urine Pharmacokinetics of 2 gram secnidazole microgranule formulation (70% drug in microgranule core) after a single oral dose administered to fasted healthy female subjects

| Parameter | Secnidazole 2 grams (N = 14) |
|---|---|
| $Ae_{0-168}$ (g) | |
| n | 14 |
| Mean (SD) | 0.306 (0.0711) |
| % CV | 23.234 |
| Geometric Mean (SD) | 0.300 (0.0602) |
| Median | 0.299 |
| Min, Max | 0.22, 0.52 |
| CLr (mL/min) | |
| n | 14 |
| Mean (SD) | 3.935 (1.0568) |
| % CV | 26.859 |
| Geometric Mean (SD) | 3.801 (1.0532) |
| Median | 3.962 |
| Min, Max | 2.23, 6.19 |
| % FE | |
| n | 14 |
| Mean (SD) | 15.300 (3.5549) |
| % CV | 23.234 |
| Geometric Mean (SD) | 14.991 (3.0081) |
| Median | 14.943 |
| Min, Max | 11.03, 26.20 |

Specific modes of administration of the pharmaceutical compositions described herein will depend on the indication. The selection of the specific route of administration and the dose regimen may be adjusted or titrated by the clinician according to methods known to the clinician in order to obtain the optimal clinical response. The amount of nitroimidazole compound to be administered may be that amount which is therapeutically effective. The dosage to be administered may depend on the characteristics of the subject being treated, e.g., the particular animal or human subject treated, age, weight, body mass index, body surface area, health, types of concurrent treatment, if any, and frequency of treatments, and can be easily determined by one of skill in the art (e.g., by the clinician).

In the embodiments described herein, the therapeutically effective amount of a nitroimidazole compound may be administered in a pharmaceutical composition. Each of the pharmaceutical compositions described herein may be used in any of the methods or dosage regimens described herein.

In some embodiments, administering a therapeutically effective amount of a nitroimidazole compound may include administering a nitroimidazole compound or a pharmaceutically acceptable salt thereof in a controlled release form. In some embodiments, the coating described herein may delay disintegration and absorption in the gastrointestinal tract and thereby providing a controlled and/or sustained action over a longer period than an immediate release composition. Additionally, such coatings may be adapted for release of a nitroimidazole compound in a predetermined pattern (e.g., in order to achieve a controlled release composition) or it may be adapted not to release the active compound until after passage of the stomach (enteric coating). Suitable coatings encompassed by such embodiments may include, but are not limited to, sugar coating, film coating (e.g., hydroxypropyl methylcellulose, methylcellulose, methyl hydroxyethyl cellulose, hydroxypropyl cellulose, carboxymethylcellulose, acrylate copolymers, polyethylene glycols and/or polyvinylpyrrolidone), or an enteric coating (e.g., methacrylic acid copolymer, cellulose acetate phthalate, hydroxypropylmethylcellulose phthalate, hydroxypropyl methylcellulose acetate succinate, polyvinyl acetate phthalate, shellac, and/or ethyl cellulose). Furthermore, a time delay material such as, for example, glyceryl monostearate or glyceryl distearate may be incorporated into the coatings of some embodiments. In still other embodiments, the coating may be adapted to protect the composition from unwanted chemical changes, for example, to reduce chemical degradation prior to the release of the active drug substance.

It is also known in the art that the active ingredients may be contained in such compositions with pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

Some embodiments are directed to methods of treating bacterial vaginosis in patient comprising administering to the patient a pharmaceutical composition as described herein. Some embodiments are directed to methods of treating bacterial vaginosis in patient comprising administering to the patient a pharmaceutical composition comprising a plurality of microgranules, wherein the microgranules comprise a core and a coating; wherein the core comprises a therapeutically effective amount of a nitroimidazole compound or pharmaceutically acceptable salt thereof; and wherein the coating surrounds the core.

In some embodiments, the nitroimidazole compound is selected from secnidazole, metronidazole, tinidazole, nimorazole, dimetridazole, 6-Amino PA824, ornidazole, megazol, azanidazole, benznidazole, pimonidazole, and combinations thereof. In some embodiments, the nitroimidazole compound is secnidazole. In some embodiments, the nitroimidazole compound comprises at least about 70% of the core by weight. In some embodiments, the nitroimidazole compound comprises about 70% of the core by weight. In some embodiments, the plurality of microgranules comprise about 1 gram to about 2 grams of the nitroimidazole compound. In some embodiments, the core further comprises at least one polymer. In some embodiments, the polymer is selected from Avicel, Methocel, hydroxyl propyl cellulose, acacia, guar gum, povidone, lactose monohydrate, and any combination thereof. In some embodiments, the core further comprises Avicel and Methocel. In some embodiments, the core further comprises Avicel pH101 and Methocel AV15LV. In some embodiments, the polymer comprises about 30% of the core by weight. In some embodiments, the coating comprises a polymer. In some embodiments, the polymer is selected from Eudagrit®, ethyl cellulose, methocel, glyceryl behenate, and any combination thereof. In some embodiments, the polymer is Eudagrit NE30D. In some embodiments, the coating further comprises a polyether polymer. In some embodiments, the polyether polymer is selected from polyethylene glycol, acetyl tributyl citrate, triethyl citrate, dibutyl phthalate, dibutyl sebacate, gelatin, propelyne glycol, triacetin, and any combination thereof. In some embodiments, the polyether polymer is PEG 4000. In some embodiments, the coating further comprises talc. In some embodiments, the coating comprises about 13% of the composition by weight. Some embodiments further comprise talc. In some embodiments, the core comprises a spheronized microgranule. In some embodiments, the core further comprises a binder.

Some embodiments are directed to a method of manufacturing a plurality of microgranules comprising a nitroimidazole compound. In some embodiments, the method of manufacturing a plurality of microgranules comprises forming a plurality of microgranule cores. In some embodiments, forming a plurality of cores comprises a wet granulation step. In some embodiments, the wet granulation step comprises mixing a nitroimidazole compound with one or more polymers to form a mixture, and hydrating the mixture to form a hydrated mixture. In some embodiments, hydrating the mixture comprises the addition of water to the mixture. In some embodiments, the wet granulation step is carried out in a planetary mixer or high shear granulator. In some embodiments, the nitroimidazole compound is secnidazole, and the one or more polymers are Avicel® pH101, Methocel® A15LV or any combination thereof.

In some embodiments, forming a plurality of microgranule cores further comprises an extrusion step. In some embodiments the hydrated mixture is passed through an extruder to form a plurality of extruded microgranule cores. In some embodiments, the hydrated mixture is passed through a Niro Extruder fitted with a 0.8 mm screen to form a plurality extruded microgranule cores.

In some embodiments, forming a plurality of microgranule cores further comprises a spheronization step to form a plurality of spheronized microgranule cores. In some embodiments, the extruded microgranule cores are spheronized to form a plurality of spheronized microgranule cores. In some embodiments, the spheronization step is carried out using a Niro Spheronizer.

In some embodiments, forming a plurality of microgranule cores further comprises drying and screening the plurality of spheronized microgranule cores. In some embodiments, the plurality of spheronized microgranule cores is dried using a Glatt fluid bed and screened to remove fines and oversize material to form a plurality of microgranule cores.

In some embodiments, the method of manufacturing a plurality of microgranules comprises coating the plurality of microgranule cores to form a plurality of coated microgranules. In some embodiments, coating the plurality of microgranule cores comprises coating the plurality of microgranule core with one or more polymers. In some embodiments, coating the plurality of microgranule cores comprises coating the microgranule core with a PEG 4000, Eudragit NE3OD and talc dispersion to form a plurality of coated microgranules. In some embodiments, the PEG 4000, Eudragit NE3OD and talc dispersion is sprayed on the plurality of microgranule cores using a Glatt fluid bed to form a plurality of coated microgranules.

Some embodiments further comprise drying and screening the plurality of coated microgranules. In some embodiments, the plurality of coated microgranules are dried in a Glatt fluid bed and screened to remove fines and oversize material.

Some embodiments further comprise blending and curing the plurality of coated microgranules. In some embodiments, blending and curing the plurality of coated microgranules comprises bending the plurality of coated microgranules with talc in a V-blender and curing in a tray dryer at 40° C. for 24 hours. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

Example 1

Experimental High Drug Loading Cores

TABLE 5

Experimental high drug loading core specifications and characteristics

| Batch # | 21155-01-39A | 21155-01-39B | 21155-01-39C |
|---|---|---|---|
| Drug load (core) | 90% | 82% | 70% |
| Avicel level | 8% | 14.6% | 26.5% |
| Binder level | 2% | 3.55% | 3.5% |
| Water Quantity | 30% | 30% | 45% |
| Yield after drying (g) | 335 | 572 | 555 |
| Fines (30 mesh) | 77.5 g (23%) | 53 g (11%) | 77 g (13.9%) |
| Retentions (16 mesh) | 2 g (0.6%) | 30 g (5.2%) | 15 g (2.7%) |
| Acceptable pellets | 253 g | 486 g | 460 g |

Experimental drug cores were prepared by the following process:

1. Wet granulation: In a planetary mixer or high shear granulator, water is sprayed on a mixture of secnidazole, Avicel pH101 and Methocel A15LV until the Methocel is completely hydrated.

2. Extrusion: The granulation is passed through a Niro Extruder fitted with a 0.8 mm screen.

3. Spheronization: The extrudates are spheronized using a Niro Spheronizer.

4. Drying and Screening: The spheres are dried in a Glatt fluid bed and screened to remove fines and oversize material.

5. Wurster coating: A PEG 4000, Eudragit NE3OD and talc dispersion is sprayed on the spheres using a Glatt fluid bed.

6. Drying and Screening: The coated spheres are dried in a Glatt fluid bed and screened to remove fines and oversize material.

7. Blending and Curing: The coated spheres are blended with talc in a V-blender and cured in a tray dryer at 40° C. for 24 hours.

Example 2

Coating of Experimental High Drug Loading Cores

Experimental high drug loading cores were coated with a PEG 4000, Eudragit NE3OD and talc dispersion. Samples were pulled after 5.1%, 6.7% and 7.9% polymer weight gain, cured at 40° C. for 24 hours and tested for dissolution. The results are shown in Table 6, with f2 values calculated relative to the profile of a drug-coated sugar sphere coated with a PEG 4000, Eudragit NE3OD and talc dispersion (control core). The 6.7% coating is closest to the clinical batch and has an acceptable f2 value.

TABLE 6

Dissolution characteristics of experimental high drug loading cores with different coating weight gain

| Time (mins) | Control core | 5.1% coat | 6.7% coat | 7.9% coat |
|---|---|---|---|---|
| | % dissolved in pH 6.8 phosphate buffer USP 1, 50 rpm | | | |
| 30 | 20 | 24 | 13 | 9 |
| 60 | 38 | 55 | 37 | 27 |
| 90 | 57 | 81 | 62 | 47 |
| 120 | 72 | 93 | 79 | 64 |
| 150 | 84 | 98 | 90 | 78 |
| 180 | 92 | 99 | 96 | 87 |
| f2 | | 39 | 63 | 52 |

What is claimed is:

1. A pharmaceutical composition comprising a plurality of microgranules,
wherein the pharmaceutical composition is for oral administration and for treating bacterial vaginosis in a subject in need thereof;
wherein each microgranule comprises a core and a coating;
wherein the core is not an inert core and comprises a mixture of an active ingredient and at least one polymer, wherein the active ingredient is secnidazole or a pharmaceutically acceptable salt thereof;
wherein secnidazole or the pharmaceutically acceptable salt thereof is present in the core and comprises at least 70% and no more than 90% of the core by weight;
wherein the coating is on the outside of the core;
wherein the plurality of microgranules comprise a therapeutically effective amount of about 1 gram to about 2 grams of secnidazole or the pharmaceutically acceptable salt thereof; and
wherein the therapeutically effective amount of secnidazole or the pharmaceutically acceptable salt thereof exhibits a maximum plasma concentration ($C_{max}$) of about 34.5 µg/ml to about 58.3 µg/ml in the subject, or a time to maximum plasma concentration ($T_{max}$) of about 3.00 hours to about 4.05 hours in the subject, or a time to drug elimination half-life ($t_{1/2}$) of about 11.3 hours to about 20.4 hours in the subject.

2. The pharmaceutical composition of claim 1, wherein secnidazole or the pharmaceutically acceptable salt thereof comprises 70% of the core by weight.

3. The pharmaceutical composition of claim 1, wherein the at least one polymer is selected from the group consisting of microcrystalline cellulose, methylcellulose, hydroxyl propyl cellulose, acacia, guar gum, povidone, lactose monohydrate, and any combination thereof.

4. The pharmaceutical composition of claim 1, wherein the core further comprises microcrystalline cellulose and methylcellulose.

5. The pharmaceutical composition of claim 1, wherein the core further comprises microcrystalline cellulose known as Avicel pH101 and methylcellulose known as Methocel AV15LV.

6. The pharmaceutical composition of claim 1, wherein the at least one polymer comprises 30% of the core by weight.

7. The pharmaceutical composition of claim 1, wherein the coating comprises a polymer.

8. The pharmaceutical composition of claim 7, wherein the polymer is selected from the group consisting of poly (meth)acrylic ester, ethyl cellulose, methylcellulose, glyceryl behenate, and any combination thereof.

9. The pharmaceutical composition of claim 7, wherein the polymer is ethyl acrylate methyl acrylate copolymer.

10. The pharmaceutical composition of claim 7, wherein the coating further comprises a polyether polymer.

11. The pharmaceutical composition of claim 10, wherein the polyether polymer is polyethylene glycol.

12. The pharmaceutical composition of claim 10, wherein the polyether polymer is PEG 4000.

13. The pharmaceutical composition of claim 1, further comprising talc.

14. The pharmaceutical composition of claim 1, wherein the coating comprises about 13% of the composition by weight.

15. The pharmaceutical composition of claim 1, wherein the coating further comprises talc.

16. The pharmaceutical composition of claim 1, wherein the core comprises a spheronized microgranule.

17. The pharmaceutical composition of claim 1, wherein the core further comprises a binder.

18. The pharmaceutical composition of claim 1, wherein the coating comprises a material selected from the group consisting of acetyl tributyl citrate, triethyl citrate, dibutyl phthalate, dibutyl sebacate, gelatin, propylene glycol, triacetin, and any combination thereof.

* * * * *